(12) United States Patent
Tacconelli

(10) Patent No.: US 11,529,327 B2
(45) Date of Patent: Dec. 20, 2022

(54) METHOD AND KIT FOR PROVIDING A CUSTOMIZABLE NAIL-BITING FINGER-SUCKING PREVENTION TREATMENT

(71) Applicant: Mark Tacconelli, Ladera Ranch, CA (US)

(72) Inventor: Mark Tacconelli, Ladera Ranch, CA (US)

( * ) Notice: Subject to any disclaimer, the term of this patent is extended or adjusted under 35 U.S.C. 154(b) by 785 days.

(21) Appl. No.: 16/433,271

(22) Filed: Jun. 6, 2019

(65) Prior Publication Data

US 2019/0374499 A1 Dec. 12, 2019

Related U.S. Application Data

(60) Provisional application No. 62/681,184, filed on Jun. 6, 2018.

(51) Int. Cl.

| *A61K 31/22* | (2006.01) |
|---|---|
| *A61M 36/00* | (2006.01) |
| *A61J 1/20* | (2006.01) |
| *A61K 31/167* | (2006.01) |
| *A61K 31/717* | (2006.01) |
| *A61K 31/45* | (2006.01) |
| *A61M 35/00* | (2006.01) |

(Continued)

(52) U.S. Cl.
CPC ............. *A61K 31/22* (2013.01); *A61J 1/2089* (2013.01); *A61K 31/045* (2013.01); *A61K 31/167* (2013.01); *A61K 31/717* (2013.01); *A61K 47/10* (2013.01); *A61K 47/12* (2013.01); *A61K 47/14* (2013.01); *A61M 35/003* (2013.01)

(58) Field of Classification Search
CPC ..... A61M 35/003; A61K 47/14; A61K 47/12; A61K 47/10; A61K 31/045; A61K 31/717; A61K 31/167; A61K 31/22; A45D 34/045; A45D 29/18; A61J 1/2089
See application file for complete search history.

(56) References Cited

U.S. PATENT DOCUMENTS

| 6,203,806 B1 * | 3/2001 | Ramin | A61P 17/16 |
| | | | 424/61 |
| 2016/0213596 A1 * | 7/2016 | Viala | A61K 8/37 |

FOREIGN PATENT DOCUMENTS

| CN | 105998544 | * 10/2016 |
| EP | 3173356 A1 | * 5/2017 |

* cited by examiner

*Primary Examiner* — Jianfeng Song
(74) *Attorney, Agent, or Firm* — Jafari Law Group, Inc.

(57) ABSTRACT

The invention relates to a method of customizing a nail-biting and/or finger sucking treatment solution, and a kit for providing a nail-biting and finger sucking treatment that is customizable for a wide range of afflicted users seeking to break a persistent nail-biting and/or finger sucking habit. In exemplary embodiments, the composition kit includes two separate containers, a first container having a nail growth-promoting, waterproofing composition that may be applied directly on a user's nails; and a second container may include an additive for customizing a bitterness factor of the first composition. Typically, the first container includes an applicator such as a brush. To facilitate adding the additive in a manner that is easily customizable, the second container may include a dropper for adding small doses of the additive composition to the first composition. The customizable kit allows the user to safely adjust the bitterness so that the treatment remains effective.

5 Claims, 5 Drawing Sheets

(51) Int. Cl.
*A61K 31/045* (2006.01)
*A61K 47/14* (2017.01)
*A61K 47/10* (2017.01)
*A61K 47/12* (2006.01)

FIG. 2
FIG. 3
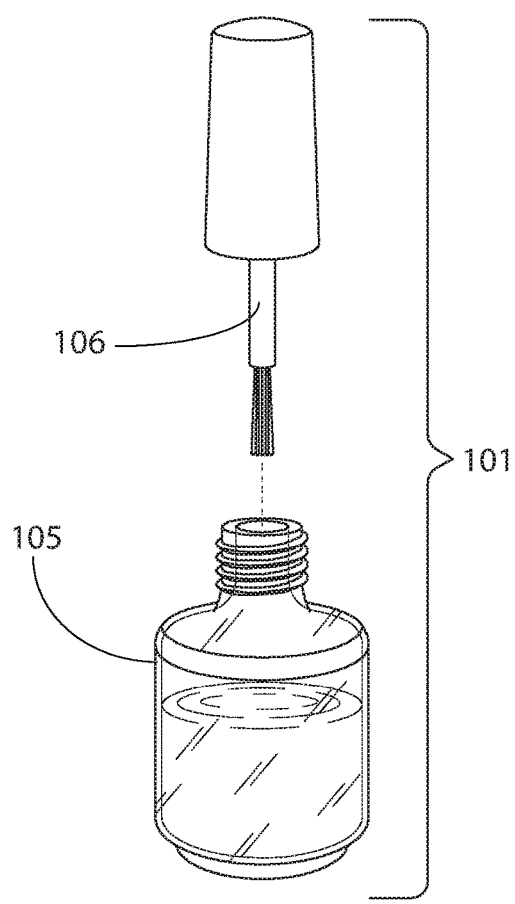
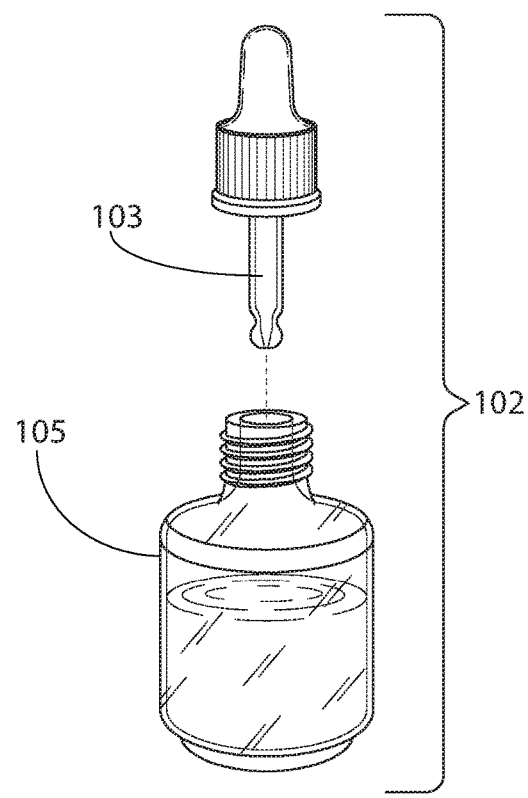

| INGREDIENT | PERCENTAGE RANGE |
|---|---|
| Butyl Acetate | 26% - 37% |
| Ethyl Acetate | 23% - 32% |
| Denatonium Benzoate | 10.2% - 20.2% |
| Nitrocellulose | 10% - 20% |
| N-Butyl alcohol | 3.8% - 9.8% |
| Isopropyl Alcohol | 2.5% - 4.5% |
| Citric Acid | .3% - .6% |

METHOD AND KIT FOR PROVIDING A CUSTOMIZABLE NAIL-BITING FINGER-SUCKING PREVENTION TREATMENT

RELATED APPLICATIONS

This application claims priority to U.S. Provisional Application No. 62/681,184, filed Jun. 6, 2018, the entire contents of which are hereby fully incorporated herein by reference for all purposes.

TECHNICAL FIELD OF THE INVENTION

The present disclosure relates generally to the field of habit breaking. More specifically, the present disclosure relates to a method for providing a customizable nail-biting and/or finger sucking prevention treatment, and kit for providing a nail-biting and/or finger sucking treatment that is customizable for a wide range of afflicted users seeking to break a persistent nail-biting and/or finger sucking habit.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever. Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Nail biting, or onychophagia, is a nervous affliction or neurosis in which a free edge of the fingernails is bitten. Onychophagia, or onychophagy, is considered a pathological oral habit and grooming disorder characterized by chronic, seemingly uncontrollable nail biting that is destructive to fingernails and the surrounding tissue including cuticles and fingers. Along with other body-focused repetitive behaviors (BFRBs), onychophagia is classified in the DSM-5 as an "Other Specified Obsessive-Compulsive and Related Disorder." Professional treatment, when necessary, focuses on both the physical and psychological factors involved in nail biting. It is sometimes described as a parafunctional activity—the common use of the mouth for an activity other than speaking, eating, or drinking. Nail biting usually leads to harmful effects to the fingers including, for example, infections. These consequences are directly derived from the physical damage of biting or from the hands becoming an infection vector. Moreover, the affliction often has a negative social impact.

In addition to nail biting, finger sucking is another common problem, which typically manifests (e.g., thumb sucking). Thumb sucking is a natural reflex for children, and sucking on thumbs, fingers, pacifiers or other objects may make babies feel secure and happy and help them learn about their world. Young children may also suck to soothe themselves and help them fall asleep. However, after permanent teeth come in, sucking may cause problems with the proper growth of the mouth and alignment of the teeth. It can also cause changes in the roof of the mouth. Pacifiers can affect the teeth essentially the same ways as sucking fingers and thumbs, but it is often an easier habit to break. The intensity of the sucking is a factor that determines whether dental problems may result. Some aggressive thumb suckers may develop problems with their baby/primary teeth as well.

Nail biting and/or finger sucking are most typically associated with early adolescence and childhood and are generally outgrown or simply stopped when the child reaches a certain age. However, it is not uncommon that onychophagia and finger sucking to continue beyond adolescence. Symptoms are both psychological and physical. People who chronically bite their nails and suck fingers may experience: distressful feelings of unease or tension prior to biting/sucking; feelings of relief or even pleasure after biting/sucking; feelings of shame, embarrassment, and guilt, often related to the appearance of physical damage to the skin and nails caused by the biting/sucking; mouth injuries, dental problems, abscesses, and infections; and, in some cases, onychophagia may lead to complicated family and social relationships. If such a habit continues much beyond early adolescence, it has an even higher potential to create several health problems, such as tense neck muscles, headaches, and even dislocation of the jaw (TMJ syndrome). Thus, if unchecked, the otherwise innocuous habit of nail biting and fingers sucking can become a serious health problem.

While the art contains several means for breaking a nail-biting and/or finger sucking habit, such as coatings and coverings for the fingernails, and the like, none of these devices has been entirely satisfactory or effective in preventing the serious problem of nail biting and/or thumb sucking, which continues into adulthood.

Some devices, for example, include complex medical devices that are placed in a user's mouth. These are undesirable because an afflicted individual seeking treatment would be forced to carry the device with them, or wear the device in public, which typically disrupts their daily social activities and often leads to the user avoiding or simply being unable to utilize the device.

Other means for breaking a nail-biting and/or finger sucking habit include compositions that may be applied to the nail in order to prevent a user from biting their nails and/or sucking their fingers. A problem with these known compositions, however, is their reliance on the bitterness effect on the user. Because bitterness is a highly personal factor, due to the fact that an individual's taste buds differ for different ages, and different individuals in general, the results of using known nail-biting prevention solutions vary so much that such known compositions are unreliable for many individuals. The problem largely persists because currently there are no solutions that are customizable to an afflicted user's taste buds.

Therefore, there is an unanticipated and inadequately addressed need for an improved nail-biting prevention treatment that is customizable for a wide range of afflicted individuals seeking to break a persistent nail-biting and/or finger sucking habits. It is to these ends that the present invention has been developed.

SUMMARY OF THE INVENTION

To minimize the limitations in the prior art, and to minimize other limitations that will be apparent upon reading and understanding the present specification, the present invention describes a method for providing a customizable nail-biting prevention treatment, and a kit for providing a nail-biting treatment that is customizable for a wide range of afflicted users seeking to break a persistent nail-biting habit.

Generally, a method of customizing a nail-biting and/or finger sucking treatment solution, and a kit for providing a nail-biting and finger sucking treatment that is customizable for a wide range of afflicted users seeking to break a persistent nail-biting and/or finger sucking habit. In exemplary embodiments, the composition kit includes two separate containers, a first container having a first composition that may be applied directly on a user's nails; the second container may include a second composition that may be used as an additive to the first composition, such that a bitterness of the first composition may be adjusted by the additive added to the first composition. Typically, the first container includes an applicator such as a brush to facilitate applying the mixture onto the user's nails. To facilitate adding the additive in a manner that is easily customizable, the second container may include a dropper for adding small doses of the additive composition to the first composition. This approach allows the user to tailor the mixture to their needs. Moreover, if a user's bitterness threshold increases, the customizable kit allows the user to safely increase the bitterness so that the treatment remains effective.

A method of customizing a nail-biting and/or finger sucking treatment solution, in accordance with some exemplary embodiments of the present invention, may include the steps of: (a) obtaining a first solution with a first bitterness level; (b) obtaining a second solution with a second bitterness level; and (c) adding at least a portion of the second solution to at least a portion of the first solution to form a combined solution with a third bitterness level, wherein the third bitterness level is greater than the first bitterness level.

In some exemplary embodiments, the first solution includes at least some of butyl acetate, ethyl acetate, denatonium benzoate, nitrocellulose, n-butyl alcohol, isopropyl alcohol, and citric acid. In some exemplary embodiments, the first solution includes the following concentrations: 31% of the butyl acetate, 28% of the ethyl acetate, 15.2% of the denatonium benzoate, 15% of the nitrocellulose, 6.8% of the n-butyl alcohol, 3.5% of the isopropyl alcohol, and 0.5% of the citric acid.

In some exemplary embodiments, the second solution includes at least some of ethyl acetate and denatonium benzoate. In some exemplary embodiments, the second solution includes the following concentrations: 80% of the ethyl acetate, and 20% of the denatonium benzoate.

A nail-biting and finger sucking treatment kit, in accordance with some exemplary embodiments of the present invention, may include: a nail growth-promoting, waterproof composition housed in a first container, the nail growth-promoting, waterproof composition including: butyl acetate, ethyl acetate, denatonium benzoate, nitrocellulose, n-butyl alcohol, isopropyl alcohol, and citric acid; a bitterness additive housed in a second container, the bitterness additive including: ethyl acetate and denatonium benzoate; and a package enclosing the first container and the second container.

A nail growth-promoting, waterproof composition, in accordance with some exemplary embodiments of the present invention, may include: 31% of the butyl acetate, 28% of the ethyl acetate, 15.2% of the denatonium benzoate, 15% of the nitrocellulose, 6.8% of the n-butyl alcohol, 3.5% of the isopropyl alcohol, and 0.5% of the citric acid.

A bitterness additive composition, in accordance with some exemplary embodiments of the present invention, may include: 80% of ethyl acetate, and 20% of denatonium benzoate.

A method of preparing a customizable nail-biting and finger sucking treatment kit, in accordance with practice of some exemplary embodiments of the present invention, may include the steps of: preparing a nail growth-promoting composition by combining between 26%-37% butyl acetate, between 23%-32% ethyl acetate, between 10.2%-20.2% denatonium benzoate, between 10%-20% nitrocellulose, between 3.8%-9.8% n-butyl alcohol, between 2.5%-4.5% isopropyl alcohol, and between 0.39%-0.69% citric acid; storing the nail growth-promoting composition in a first container, the first container having a brush applicator; preparing a bitterness additive by combining between 70%-90% ethyl acetate, and between 10%-30% denatonium benzoate; storing the bitterness additive in a second container; packaging the first container including the nail growth-promoting composition and the second container including the bitterness additive in a single package.

Various objectives and advantages of the present invention will become apparent from the following description taken in conjunction with the accompanying drawings wherein are set forth, by way of illustration and example, certain embodiments of this invention. The drawings submitted herewith constitute a part of this specification, include exemplary embodiments of the present invention, and illustrate various objects and features thereof.

BRIEF DESCRIPTION OF THE DRAWINGS

The method for providing a customizable nail-biting and/or finger sucking prevention treatment and kit, as disclosed herein, are further described in terms of exemplary embodiments. These exemplary embodiments are described in detail with reference to the drawings, which have not necessarily been drawn to scale in order to enhance their clarity and improve understanding of the various embodiments of the invention. Furthermore, elements that are known to be common and well understood to those in the industry are not depicted in order to provide a clear view of the various embodiments of the invention. These embodiments are non-limiting exemplary embodiments, in which like reference numerals represent similar structures throughout the several views of the drawings. The drawings that accompany the detailed description can be briefly described as follows:

FIG. 2 illustrates a perspective view of a first composition container, including a brush applicator, in accordance with exemplary embodiments of the present invention.

FIG. 3 illustrates a perspective view a dropper that may be used to apply drops or small amounts of a bitterness additive to customize a treatment, in accordance with exemplary embodiments of the present invention.

DETAILED DESCRIPTION OF THE INVENTION

Figure 1:
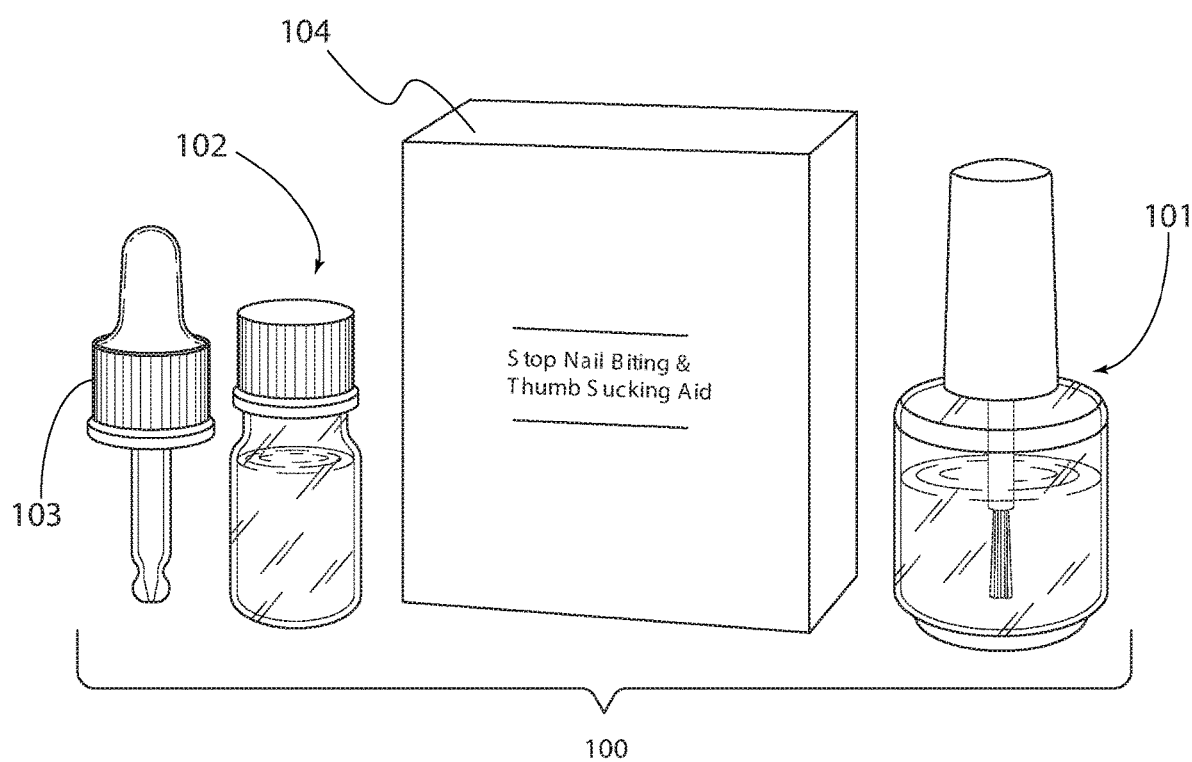
FIG. 1 illustrates a perspective view of a kit in accordance with the present invention.

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized, and changes may be made without departing from the scope of the invention. Wherever possible, the same reference numbers are used in the drawings and the following description to refer to the same or similar elements.

In the following detailed description, numerous specific details are set forth by way of examples in order to provide a thorough understanding of the relevant teachings. However, it should be apparent to those skilled in the art that the present teachings may be practiced without such details. In other instances, well known compositions, structures, components and/or functional or structural relationship thereof, etc., have been described at a relatively high-level, without detail, in order to avoid unnecessarily obscuring aspects of the present teachings.

Throughout the specification and claims, terms may have nuanced meanings suggested or implied in context beyond an explicitly stated meaning. Likewise, the phrase "in one embodiment/example" as used herein does not necessarily refer to the same embodiment and the phrase "in another embodiment/example" as used herein does not necessarily refer to a different embodiment. It is intended, for example, that claimed subject matter include combinations of example embodiments in whole or in part.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and or steps. Thus, such conditional language is not generally intended to imply that features, elements and or steps are in any way required for one or more embodiments, whether these features, elements and or steps are included or are to be performed in any particular embodiment.

The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present. The term "and or" means that "and" applies to some embodiments and "or" applies to some embodiments. Thus, A, B, and or C can be replaced with A, B, and C written in one sentence and A, B, or C written in another sentence. A, B, and or C means that some embodiments can include A and B, some embodiments can include A and C, some embodiments can include B and C, some embodiments can only include A, some embodiments can include only B, some embodiments can include only C, and some embodiments include A, B, and C. The term "and or" is used to avoid unnecessary redundancy. Similarly, terms, such as "a, an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

While exemplary embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the invention or inventions disclosed herein. Accordingly, the following detailed description does not limit the disclosure. Instead, the proper scope of the disclosure is defined by the appended claims.

The present disclosure relates to, among other things, a method and kit for providing a customizable nail-biting and/or finger sucking prevention treatment. Exemplary embodiments of the present disclosure are described with reference to the drawings for illustration purposes and are not intended to limit the scope of the present disclosure.

As mentioned above, with regard to individuals' taste buds, sensitivity to bitterness is highly personal and can change over time. Moreover, even to a single individual, their perception of tasting something bitter often changes throughout their lifetime, because the sensitivities of their taste buds may differ at different ages. Accordingly, current nail-biting and/or finger sucking solutions often fail because their bitterness levels may be too low and their compositions cannot be customized. With this in mind, the present invention provides a system and method to tailor the bitterness factor of the nail biting and/or finger sucking treatment to each individual of any age for which the customizable treatment may be safe to use.

As will be described in detail below, the present invention requires no equipment at all, and may be implemented by any individual on the spot. This customizable approach allows an afflicted individual to tailor the treatment to their needs and avoid experimentation with different product versions or types.

In general, a kit in accordance with the present invention may enable the bitterness level of a nail-biting and/or finger sucking treatment solution to be increased to accommodate people with varying (e.g., higher) thresholds for bitterness. To this end the kit may typically include 1) a base solution that may comprise a nail growth-promoting and waterproofing composition, and that may also include a baseline level of bitterness, and 2) a separate and distinct second bitterness solution (e.g., an additive solution) that may be added to the base solution to increase the resultant overall solution's bitterness level. It may be preferable that the additive solution include a sufficiently high level of bitterness so that the addition of small amounts of the additive solution to the base solution may increase the overall bitterness level of the overall and combined solutions. In this way the bitterness additive may be added to the nail growth-promoting, waterproofing composition one drop at a time, and the one or more drops of additional bitterness solution may increase the repulsive bitter taste to a level that may stop the nail-biting and/or finger sucking habits of people with higher bitterness thresholds.

Turning now to the figures, FIG. 1 illustrates a perspective view of a kit in accordance with the present invention. More specifically, FIG. 1 depicts kit 100, which includes generally a nail growth-promoting, waterproofing composition 101 (e.g., the base solution) housed in a first container, a bitterness additive 102 (e.g., the additive solution) housed in a second container, a dropper 103 generally configured to draw at least a drop of the bitterness additive 102 from the second container; and a package 104 that encloses or contains each of the nail growth-promoting, waterproofing composition 101 within the first container 101 and the bitterness additive 102 within the second container.

The nail growth-promoting waterproofing composition 101 may generally comprise at least some of butyl acetate, ethyl acetate, denatonium benzoate, nitrocellulose, n-butyl alcohol, isopropyl alcohol, and citric acid. The combined ingredients may result into a substance that may be applied to a person's fingernails. The Butyl Acetate and Ethyl Acetate may provide the liquid base for the nail growth-promoting composition and may be primarily used as solvents to keep the nail growth-promoting composition thin, quick drying, and low in odor.

Denatonium is a bitter chemical compound, usually existing in the form of Denatonium Benzoate, that may have a bitterness threshold of 0.05 ppm for the benzoate. In one exemplary embodiment hereof, the level of Denatonium Benzoate included in the base solution 101 may provide a baseline bitterness level of the solution. As will be described in further detail in other sections, this baseline level of bitterness may be used as-is, and/or may be increased by adding portions of the additive solution 102 to the base solution 101. Safe levels for consumption in case of accidental human swallowing should be kept in mind when packaging or storing the solutions 101, 102 in respective containers. In addition, as will be discussed further below, the bitterness additive 101 may also include this ingredient.

Nitrocellulose may be a main ingredient (cellulose nitrate) of the nail growth-promoting composition known for creating a film that holds together other substances. In the case of the nail growth-promoting composition, this ingredient may be used to create a film that may provide a thin membrane to allow at least a portion of the applied Denatonium Benzoate to be contacted during licking, sucking or biting of the fingers and/or nails.

N-Butyl Alcohol is typically used primarily to dissolve other substances in cosmetic product formulations, and in the present invention may be used as a thinner of the nail growth-promoting composition so that the composition may dry quickly. Similarly, Isopropyl Alcohol also promotes quicker drying when the composition is applied to a user's nail.

Citric Acid is a stabilizing agent produced from the fermentation of sugar cane that may be used to control the color of the pigment of the base and/or combined solutions. In the preset invention, Citric Acid may be used to keep the nail growth-promoting composition clear or translucent.

The bitterness additive 102 may generally comprise at least some of Ethyl Acetate and Denatonium Benzoate. With respect to the bitterness additive 102, the Ethyl Acetate may be used to keep the Denatonium Benzoate in liquid form, since Denatonium Benzoate may usually exist in crystal form. Ethyl Acetate may also be used to allow the Denatonium Benzoate to mix easily and blend with the nail growth-promoting, waterproofing composition 101 when the additive solution 102 may be added to the base solution 101. However, Ethyl Acetate is highly flammable and toxic when ingested, and can cause irritation when it comes into contact with the eyes or skin. Accordingly, as will be described in other sections, the levels of Ethyl Acetate and Denatonium Benzoate included in the bitterness additive 102 must be specifically designed to maximize the bitterness concentration in the liquid form while minimizing the flammability and toxicity potential of the solution.

Accordingly, in exemplary embodiments, a nail-biting and/or finger sucking treatment kit 100 may include a nail growth-promoting, waterproofing composition 101 housed in a first container, the nail growth-promoting composition 101 including: butyl acetate, ethyl acetate, denatonium benzoate, nitrocellulose, n-butyl alcohol, isopropyl alcohol, and citric acid; a bitterness additive 102 housed in a second container, the bitterness additive 102 including: ethyl acetate and denatonium benzoate; and a package 104 enclosing the first container storing the nail growth-promoting, waterproofing composition 101 and the second container storing the bitterness additive 102.

In some exemplary embodiments, as will be discussed with reference to the next figure in turn, the first container may include a brush applicator to facilitate applying the nail growth-promoting, waterproofing composition 101 onto a user's nails.

Turning now to the next figure, FIG. 2 illustrates a perspective view of a first composition container, including a brush applicator, in accordance with exemplary embodiments of the present invention. More specifically, FIG. 2 illustrates a perspective view of container 105 that may include the nail growth-promoting composition 101, container 105 typically a glass container or the like. In this embodiment, container 105 includes a brush applicator 106 as mentioned above for facilitating application of the nail growth-promoting, waterproofing composition 101 to the user's fingernails.

Next, FIG. 3 illustrates a perspective view of a dropper 103 that may be used to add drops or small amounts of the bitterness additive 102 to the base solution 101 in order to customize a treatment, in accordance with exemplary embodiments of the present invention. More specifically, FIG. 3 illustrates a perspective view of a dropper 103 that may be used to add drops or small amounts of the bitterness additive 102 into the container 105 (that is, into the base solution 101). As will be discussed further below, this allows a user to customize the bitterness of their treatment.

Figure 4:
FIG. 4 illustrates a table of ingredients for a first composition included in a kit according to some exemplary embodiments of the present invention.

Now turning to FIG. 4, a table of ingredients for a first composition included in a kit is shown, according to some exemplary embodiments of the present invention. More specifically, FIG. 4 depicts Table 400 disclosing a list of ingredients for a nail growth-promoting waterproofing composition 101 that may be used as a base to which the bitterness additive 102 (see Table 500 in FIG. 5 below) may be added as discussed in this disclosure.

As mentioned above, the primary ingredients of Butyl Acetate, Ethyl Acetate, Denatonium Benzoate, Nitrocellulose, N-Butyl alcohol, Isopropyl Alcohol, and Citric Acid may be used to prepare the nail growth-promoting and waterproofing composition 101. As may be appreciated by a person of ordinary skill in the art, different formulations or percentages of the primary ingredients may give different user properties (i.e. stickiness, drying time, smell, coating thickness, shine, and/or pliability), some of which will be discussed in turn.

In some exemplary embodiments, the nail growth-promoting waterproofing composition 101 may include the following concentrations of the butyl acetate, the ethyl acetate, the denatonium benzoate, the nitrocellulose, the n-butyl alcohol, the isopropyl alcohol, and the citric acid: between 26%-37% butyl acetate, between 23%-32% ethyl acetate, between 10.2%-20.2% denatonium benzoate, between 10%-20% nitrocellulose, between 3.8%-9.8% n-butyl alcohol, between 2.5%-4.5% isopropyl alcohol, and between 0.39%-0.69% citric acid.

In some exemplary embodiments, the nail growth-promoting, waterproofing composition 101 may include the following concentrations of the butyl acetate, the ethyl acetate, the denatonium benzoate, the nitrocellulose, the n-butyl alcohol, the isopropyl alcohol, and the citric acid: 31% of the butyl acetate, 28% of the ethyl acetate, 15.2% of the denatonium benzoate, 15% of the nitrocellulose, 6.8% of the n-butyl alcohol, 3.5% of the isopropyl alcohol, and 0.5% of the citric acid. It has been discovered that this formulation may provide the lowest detectable smell, the fastest drying, the most translucent, the highest shine, and an adequate baseline bitterness level for many users.

Figure 5:
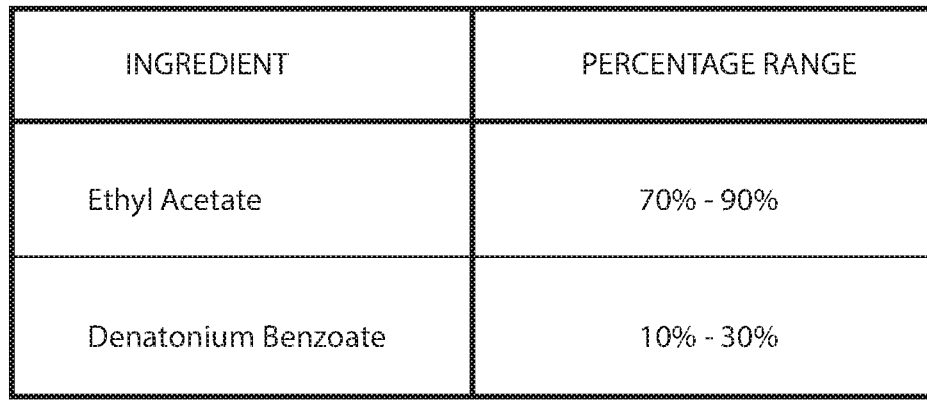
FIG. 5 illustrates a table of ingredients for a second composition included in a kit according to some exemplary embodiments of the present invention.

The next figure, FIG. 5, illustrates a table of ingredients for a second composition included in a kit according to some exemplary embodiments of the present invention. More specifically, FIG. 5 depicts Table 500 disclosing a list of ingredients for a bitterness additive 102 in accordance with the present invention, from which drops may be taken to add to a nail growth-promoting, waterproofing composition 101 so that a user may customize a bitterness level suitable for their bitterness threshold, in order to maximize the effectiveness of their customized treatment.

As mentioned above, the ingredients of Ethyl Acetate and Denatonium Benzoate may make up the bitterness additive 102 in accordance with the present invention. In addition, Ethyl Acetate is highly flammable and toxic when ingested, and can cause irritation when it comes into contact with the eyes or skin. Accordingly, the levels of Ethyl Acetate and Denatonium Benzoate included in the bitterness additive 102 must be specifically designed to maximize the bitterness concentration of the additive 102 while minimizing the solution's flammability and toxicity dangers. In some exemplary embodiments, the bitterness additive 102 may include the following concentrations of the ethyl acetate and the denatonium benzoate that may optimize the additive's bitterness concentration while minimizing the potential danger of the additive 102 due to its potential flammability and toxicity: 80% of the ethyl acetate, and 20% of the denatonium benzoate. In some exemplary embodiments, the concentrations for these ingredients may range between 70%-90% for the Ethyl Acetate, and between 10%-30% for the denatonium benzoate. In some exemplary embodiments, the concentrations for these ingredients may range between 75%-85% of the ethyl acetate, and between 15%-25% for the denatonium benzoate.

It should be noted that the levels of Butyl Acetate, Ethyl Acetate and/or Citris Acid in the base solution 101 as described above are specifically designed to allow the base solution 101 to receive and accommodate the additional Ethyl Acetate and additional Denatonium Benzoate from the additive solution 102 while preserving the desired attributes and characteristics of the overall combined solution. For example, the levels of Butyl Acetate, Ethyl Acetate and/or Citric Acid in the base solution 101 may be designed to help to ensure that the combined solution continue to be low in odor, to be fast drying and to remain sufficiently clear even while the levels of Ethyl Acetate and Denatonium Benzoate are increased with the addition of the bitterness additive 102.

In creating a kit for consumers, the compositions or solutions 101, 102 mentioned above may be packaged as shown in FIG. 1 so as to provide the user with everything they may need to customize their treatment. Accordingly, a method of preparing a customizable nail-biting and/or finger sucking treatment kit, in accordance with exemplary embodiments of the present invention, may include the steps of: preparing a nail growth-promoting, waterproofing composition by combining between 26%-37% butyl acetate, between 23%-32% ethyl acetate, between 10.2%-20.2% denatonium benzoate, between 10%-20% nitrocellulose, between 3.8%-9.8% n-butyl alcohol, between 2.5%-4.5% isopropyl alcohol, and between 0.39%-0.69% citric acid; storing the nail growth-promoting composition in a first container, the first container having a brush applicator; preparing a bitterness additive by combining between 70%-90% ethyl acetate, and between 10%-30% denatonium benzoate; storing the bitterness additive in a second container; packaging the first container including the nail growth-promoting, waterproofing composition and the second container including the bitterness additive in a single package.

In some exemplary embodiments, preparing the nail growth-promoting, waterproofing composition 101 may comprise combining 28% of the ethyl acetate, and 15.2% of the denatonium benzoate. This may provide a baseline bitterness level of the base solution 101. In some exemplary embodiments, preparing the bitterness additive 102 may comprise combining 80% of the ethyl acetate, and 20% of the denatonium benzoate to optimize the additive's bitterness concentration while minimizing its flammability and/or toxicity.

In some exemplary embodiments, packaging the composition 101 and additive 102 may further comprise including a dropper 103, configured to draw at least a drop of the bitterness additive 102 from the second container to be added to the base solution 101 in the first container.

Figure 6:
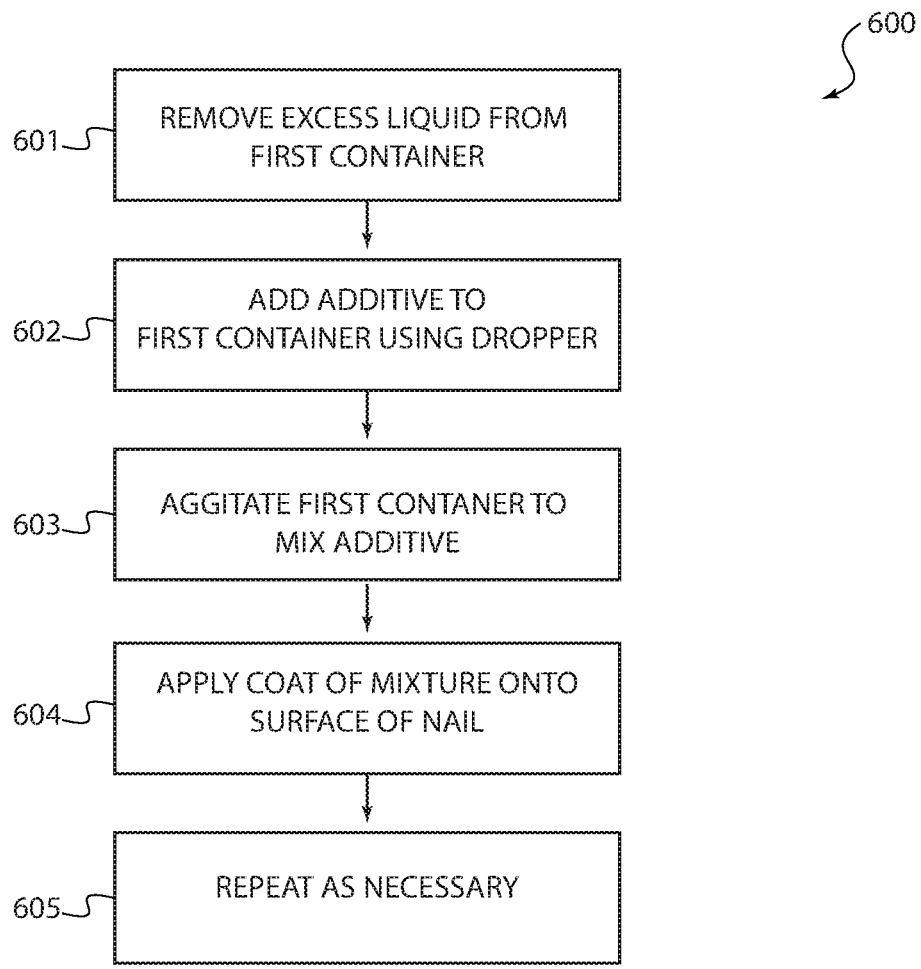
FIG. 6 illustrates a flow chart depicting a method of customizing a treatment in accordance with practice of some exemplary embodiments of the present invention.

The next figure, FIG. 6, illustrates a flow chart depicting a method of customizing a treatment in accordance with practice of some exemplary embodiments of the present invention. More specifically, FIG. 6 depicts method 600 for customizing a treatment. Although method 600 is exemplarily shown with a series of steps in one particular sequence, method 600 may include fewer or more steps in alternative sequences without deviating from the scope of the present invention. As will be described in greater detail below, method 600 of customizing a treatment may include steps 601-605. Prior to performing steps 601-605, it is understood that the user may have tested the baseline bitterness level of the base solution 101 and may have determined that the baseline bitterness level may be too low, and that customization may be required.

In step 601, a user may open a cap of a first container storing a nail growth-promoting, waterproofing composition and place the cap aside. In this step, the user may ensure that there is adequate room in the container for additional liquid. In practice of some exemplary embodiments, the user may be required (and or instructed) to dip a brush applicator into the container, and then brush some the composition liquid on a paper towel a few times to remove the liquid from the container in order to make room for the additional bitter additive.

In step 602, with the container having the composition near full, a user may add 1 or 2 drops of the bitter additive into the neck of the container. If less than a full container, a user may be required (and or instructed) to add 1 drop at a time.

In step 603, the user may simply replace the container's cap and agitate the container, or otherwise shake the same vigorously for 5-10 seconds.

In step 603, the user may apply a coat of the mixture onto a surface of his/her fingernail to test it. After the solution may dry, the user may taste the dried composition to confirm that the newly increased bitterness level meets their threshold so as to be a deterrent to their habitual nail-biting and/or finger sucking ailment.

If necessary, in step 605, steps 601-604 may be repeated as necessary to again increase the level of bitterness. Once the proper bitterness threshold is reached, the user may begin using the customized formula to begin their custom treatment. Care needs to be taken as to provide a proper bitter disincentive for nail-biting and finger sucking. For example, too much bitterness, and the polish can overwhelm the biter, make eating difficult, or make him/her sick to the stomach, which may cause the user to remove the composition and thus end treatment. In another example, inadequate levels of bitterness may not deter the user from biting his/her nails and/or sucking his/her fingers. In this way, the customizable treatment kit 100 may allow for the user to optimize the bitterness for his/her specific bitterness threshold.

Referring back to step 602, a user may add one or more drops of the additive solution 102 to the base solution 101 in order to increase the base solution's level of bitterness. In one example of this, one drop of the additive solution 102 may include approximately 0.05 ml of the liquid solution. Using the concentration numbers described above, if the additive solution 102 contains 20% denatonium benzoate, then one drop may contain 20% of 0.05 ml or 0.01 ml of denatonium benzoate. In addition, in one example, the bottle 105 may contain approximately 15 ml of total base solution 101. If the baseline solution includes 15.2% of denatonium benzoate, then the baseline solution 101 may include approximately 15.2% of 15 ml or 2.28 ml of denatonium benzoate. Thus, adding one drop or 0.01 ml of denatonium benzoate to the base solution 101 may increase the total amount of denatonium benzoate from 2.28 ml to 2.29 ml or by approximately 0.4%. And because denatonium benzoate may be extremely bitter, this added percentage may effectively increase the overall bitterness level of the combined solution. Note however that multiple drops of the additive 102 may need to be added to the base solution 101 to achieve the desired level of bitterness.

Figure 7:
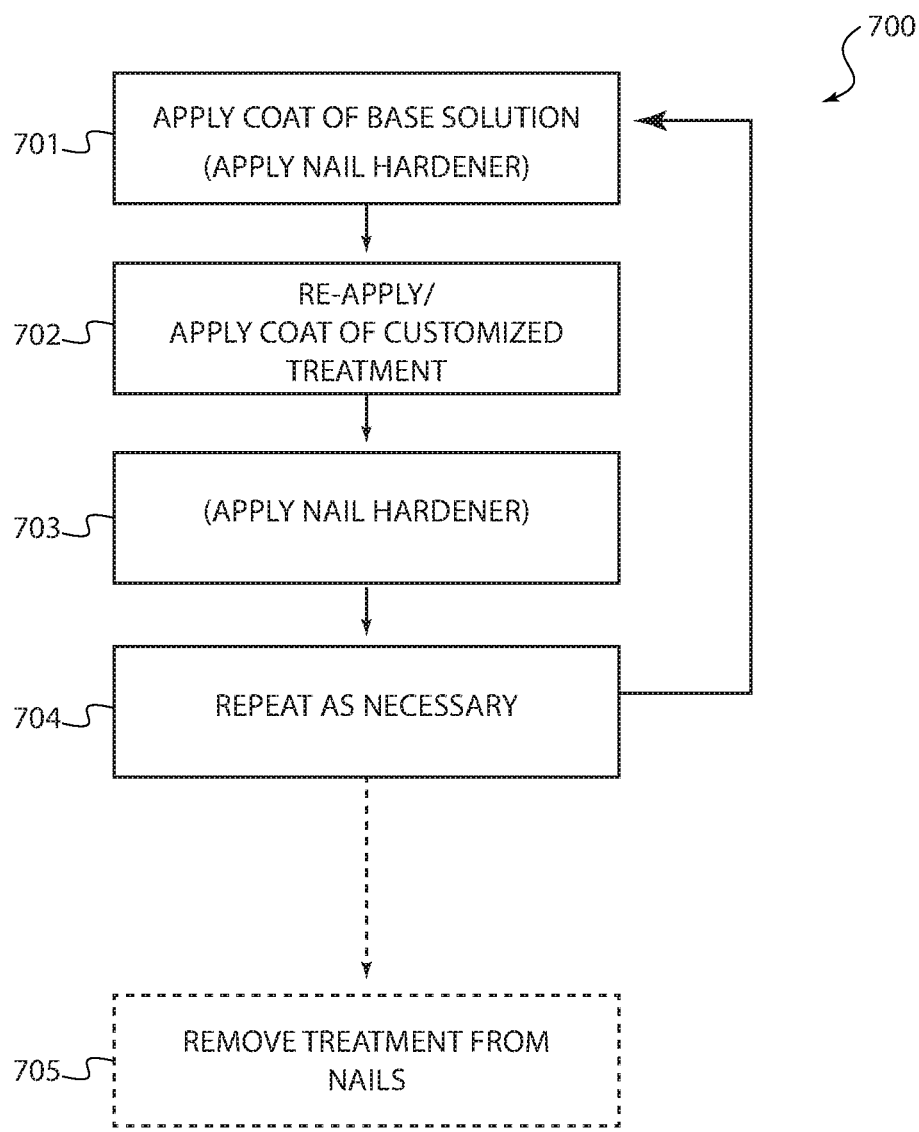
FIG. 7 illustrates a flow chart depicting a method of applying a customized treatment in accordance with practice of some exemplary embodiments of the present invention.

Turning now to the last figure, FIG. 7 illustrates a flow chart depicting a method of applying a customized treatment in accordance with practice of some exemplary embodiments of the present invention. More specifically, FIG. 7 depicts method 700 for applying a customized treatment. Although method 700 is exemplarily shown with a series of steps in one particular sequence, method 700 may include fewer or more steps in alternative sequences without deviating from the scope of the present invention. As will be described in greater detail below, method 700 for applying a customized treatment may include steps 701-705.

In step 701, a user may apply one coat of the base solution 101 and/or the customized treatment they have previously tested and prepared (e.g., by following steps 601-605). In this step, a user preferably applies the coat of the customized treatment to clean, dry nails either alone or over polish and allow it to dry completely. In exemplary embodiments, this is performed twice a week. For stubborn or "high tolerance" biters, this application may be performed more frequently as needed or even daily. There is no limit to composition application per se, and repetitive applications may depend on the customized, individual composition and the strength of the user's urge to bite.

Accordingly, in step 702, a user should re-apply within the week of the first application, and similarly and preferably applying the coat of the customized treatment to clean, dry nails allowing it to dry completely.

In some exemplary embodiments, a step 703 may be implemented, in which application of a nail hardener may be employed. Note that the step 703 may also be performed prior to starting steps 701-705 (that is, a nail hardener may be applied first). Accordingly, in some kits in accordance with the present invention, a nail hardener may be included, for example along with the other contents in or with package 104 as shown in FIG. 1.

In step 704, the process or steps 701-703 above may be repeated as necessary, until the afflicted user has successfully broken the habit of biting their nails. Upon initial application, the bitter taste will be most intense, but washing the user's nails with soap and water may reduce the bitterness slightly.

If no longer required, or simply desiring to remove the customized mixture, at step 705, or at any time, a user may remove the customized mixture with commercially available nail polish remover. Accordingly, in some kits in accordance with the present invention, a nail polish remover may be included, for example along with the other contents in or with package 104 as shown in FIG. 1.

It is understood that a combination of the steps 601-605 and the steps 701-705 may be performed at any time. For example, after performing some or all of the steps 701-705, the user may decide that their bitterness level is inadequate, and he/she may choose to further customize the bitterness level of their treatment solution by repeating steps 601-605 or any portion thereof.

In another exemplary embodiment hereof, the base solution 101 may include a lesser amount of denatonium benzoate in order to provide a less bitter baseline bitterness level. As stated in other sections, sensitivities to bitterness may vary greatly from person to person, and in fact, some may have a very low tolerance for bitterness. In this case, it may be that the baseline bitterness level of the base solution 101 as described above may be too bitter for the person with a low tolerance to bitterness. This may cause problems with eating, upset stomachs and even vomiting. Accordingly, for persons with low bitterness tolerance, it may be preferable that the baseline bitterness level of the base solution 101 be less so that he/she may start the process of testing and customizing the treatment solution at an initially lower bitterness level.

For example, in some exemplary embodiments hereof, the level of denatonium benzoate may be three-quarters (e.g., 7.65%-15.15%), one-half (e.g., 5.1%-10.1%), one-quarter (e.g., 2.55-5.05%), or any other amount lower than the level of denatonium benzoate described in prior embodiments. In this way, the user may start with a base solution 101 with a very low level of bitterness and subsequently add the bitter additive 102 to increase the level to their desired level. Note that the bitterness level arrived at after adding the additive 102 may be below or above the bitterness baseline level of the base solution 101 in other embodiments.

In another exemplary embodiment hereof, the base solution 101 may contain no denatonium benzoate such that the baseline bitterness level may approach zero. In this case, the user may simply begin the process by adding small amounts of the bitterness additive 102 to the base solution 101, testing the results, and repeating the process until the desired level of bitterness is achieved. This may ensure that a person with a very low tolerance to bitterness may be enabled to successfully customize a treatment solution by creating a solution that may have a very low, yet still sufficient, level of bitterness.

The benefits of the nail-biting and/or finger sucking treatment kit 100, the base solution 101 and the bitterness additive solution 102 are multifold, and may include, without limitation, the following benefits.

First, the treatment kit 100 enables persons with a high tolerance for bitterness to customize their treatment solution by increasing the solution's bitterness level. As described, this may be accomplished by adding one or more drops of the bitterness additive 102 to the base solution 101.

Second, the treatment kit 100 enables persons with a low tolerance for bitterness to start with a lower level of bitterness and gradually increase the bitterness level of their solution until the level meets their needs. As described, this may be accomplished by beginning with a base solution 101 that includes a low baseline bitterness level and adding one or more drops of the bitter additive 102 to the base solution 101.

Third, the bitterness additive 102 may be specifically designed to optimize its bitterness concentration while minimizing the dangers associated with the flammability and toxicity of the active Ethyl Acetate ingredient.

Fourth, the base solution may include ingredients in specifically designed concentrations and/or ranges that will allow the base solution 101 to receive amounts of the bitterness additive 102 while preserving the solution's desired characteristics (e.g., low odor, fast drying, sufficiently clear, etc.).

It is clear that the benefits described above may enable a person who would otherwise be unsuccessful in treating their nail biting and/or finger sucking affliction when using a standard solution treatment to instead be successful in treating his/her affliction by using the customized treatment solution.

It is understood by a person of ordinary skill in the art, upon reading this specification, that any of the elements or details of any of the embodiments described herein or otherwise may be combined in any way, and that the scope of the invention includes any combinations of any elements or details of any of the embodiments hereof.

The foregoing detailed description has set forth various embodiments of the nail-biting and/or finger sucking solution, including a kit, devices and/or processes, by the use of diagrams, flowcharts, and/or examples. The subject matter described herein sometimes illustrates different compositions or variations thereof. It is to be understood that such depicted options are merely exemplary, and that in fact many other variations may be implemented which achieve the same functionality. With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

A method for providing a customizable nail-biting and/or finger sucking prevention treatment, and kit for providing a nail-biting and/or finger sucking treatment has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

What is claimed is:

1. A customizable nail-biting treatment and finger sucking kit, comprising:
   a nail growth-promoting, waterproofing composition housed in a first container, the nail growth-promoting, waterproofing composition including: 31% butyl acetate, 28% ethyl acetate, 15.2% denatonium benzoate, 15% nitrocellulose, 6.8% n-butyl alcohol, 3.5% isopropyl alcohol, and 0.5% citric acid;
   a bitterness additive housed in a second container, the bitterness additive including: ethyl acetate and denatonium benzoate; and
   a package enclosing the first container and the second container.

2. The customizable nail-biting and finger sucking treatment kit of claim 1, wherein the bitterness additive includes the following concentrations of the ethyl acetate and the denatonium benzoate:
   80% of the ethyl acetate, and
   20% of the denatonium benzoate.

3. The customizable nail-biting treatment and finger sucking treatment kit of claim 1, wherein the bitterness additive includes the following concentrations of the ethyl acetate and the denatonium benzoate:
   between 75%-85% of the ethyl acetate, and
   between 15%-25% of the denatonium benzoate.

4. The customizable nail-biting treatment and finger sucking treatment kit of claim 1, further comprising a dropper configured to draw at least a drop from the second container, the dropper enclosed in the package along with the first and second containers.

5. The customizable nail-biting treatment kit of claim 1, wherein the first container comprises a brush applicator.

* * * * *